United States Patent [19]

Yamanaka et al.

[11] Patent Number: 5,318,883
[45] Date of Patent: Jun. 7, 1994

[54] CHARGE CONTROL AGENT AND TOWER FOR DEVELOPING ELECTROSTATIC IMAGES

[75] Inventors: Schunichiro Yamanaka, Hirakata; Kazuaki Sukata, Yawata; Shuji Sugawara, Neyagawa, all of Japan

[73] Assignee: Orient Chemical Industries, Ltd., Osaka, Japan

[21] Appl. No.: 886,956

[22] Filed: May 21, 1992

[30] Foreign Application Priority Data

May 23, 1991 [JP] Japan ............... 3-149854

[51] Int. Cl.$^5$ .................................. G03G 9/097
[52] U.S. Cl. ........................................ 430/110
[58] Field of Search ................ 430/106, 109, 110

[56] References Cited

U.S. PATENT DOCUMENTS 4,206,064  6/1980  Kiuchi .
4,656,112  4/1987  Kawagishi .

FOREIGN PATENT DOCUMENTS

| 0385580 | 1/1990 | European Pat. Off. ..... G03G 9/097 |
| 254738 | 3/1988 | Fed. Rep. of Germany ......... C08K 5/15 |
| 254740 | 3/1988 | Fed. Rep. of Germany ......... C08K 5/15 |
| 273844 | 11/1989 | Fed. Rep. of Germany ......... C08K 5/13 |
| 41-2427 | 2/1941 | Japan .................. 103K/112 |
| 41-20153 | 11/1941 | Japan .................. 103K/112 |
| 43-17955 | 7/1943 | Japan .................. 103K/112 |
| 45-26478 | 9/1970 | Japan .................. 103K/112 |
| 63-099031 | 4/1988 | Japan .................. C07C 39/17 |
| 63-138357 | 6/1988 | Japan .................. G03G 9/08 |
| 63-206769 | 8/1988 | Japan .................. G03G 9/08 |
| 63-266462 | 11/1988 | Japan .................. G03G 9/08 |
| 2-201378 | 8/1990 | Japan .................. G03G 0/097 |
| 2-291569 | 12/1990 | Japan .................. G03G 9/09 |

OTHER PUBLICATIONS

Gutsche et al. Calixarenes. 4. The Synthesis, Characterisation, and Properties of the Calixarenes from p-tert-Butylphenol-J.Am.Chem.Soc. 1981 103, 3782-3792.
Shinkai Calixarenes as a new functionalized host molecules-Pure & Apl. Chem. vol. 58, No. 11 pp. 1523-1528, 1986.
Shinkai et al. A New Synthesis of p-Nitrocalix6-]Arene-Tetrahedron Letters vol. 26, No. 28 pp. 3343-3344, 1985.
Kagaku -182, 14-23 (1986).

*Primary Examiner*—John Goodrow
*Attorney, Agent, or Firm*—McGlew and Tuttle

[57] ABSTRACT

A charge control agent whose active ingredient is a calix(n)arene compound represented by formula [I]:

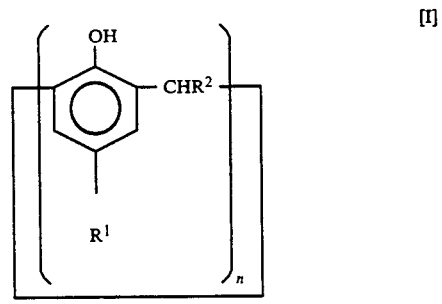

wherein
 $R^1$ represents an alicyclic group;
 $R^2$ represents a hydrogen atom, an alkyl group having 1 to 4 carbon atoms or an aryl group; and
 n represents an integer of 1 to 8, is provided, which can be incorporated into a toner for developing electrostatic images.

17 Claims, 1 Drawing Sheet

CHARGE CONTROL AGENT AND TOWER FOR DEVELOPING ELECTROSTATIC IMAGES

BACKGROUND OF THE INVENTION

1. Field of the Invention

The present invention relates to a toner for developing electrostatic images used for electrophotography, electrostatic recording, electrostatic printing and other purposes, and a charge control agent capable of controlling the amount of charges of the toner.

2. Description of the Prior Art

In copying machines and other apparatuses based on electrophotography, various dry or wet toners containing a coloring agent, a fixing resin and other substances are used to visualize (develop) the electrostatic latent image formed on the photoreceptor having a light-sensitive layer containing an inorganic or organic photoconductive substance.

The chargeability of such toners is the most important factor in electrostatic latent image developing systems. Thus, to appropriately control the charge amount of toner, a charge control agent providing a positive or negative charge is often added to the toner.

Examples of charge control agents providing a positive charge for toner in actual application include the nigrosine dyes disclosed in Japanese Patent Provisional Publication No. 2427/1966 and other publications. Examples of charge control agents providing a negative charge for toner include the metal complex dyes described in Japanese Patent Examined Publication Nos. 20153/1966, 17955/1968 and 26478/1970 and other publications.

However, most of the above-mentioned charge control agents have a complex structure and their stability is low. For example, they are liable to decompose or deteriorate to lose their charge control performance due to mechanical friction and impact, changes in temperature or humidity, electric shocks, light irradiation and other causes. In addition, most of them have been relatively densely colored, thus lacking versatility for use in color toners.

In recent years, various charge control agents free of such problems have been disclosed, including the metal complexes of salicylic acid or derivatives thereof disclosed in U.S. Pat. Nos. 4,206,064 and 4,656,112, and the metal complexes of aromatic oxyaldehydes disclosed in Japanese Patent Provisional Publication No. 206769/1988.

However, these charge control agents are insufficient with respect to resin affinity, dispersibility, etc., and in addition, they comprise a compound containing a heavy metal such as chromium, cobalt, copper or zinc; most of them involve a problem in safety or hygiene to the human body.

On the other hand, there are known toners supplemented with various phenol compounds for the purpose of improving the fixability and offset property of the toner or preventing the deterioration of a surface-treated carrier. For example, Japanese Patent Provisional Publication No. 138357/1988 discloses a toner containing an oligomer of a phenol compound having an alkyl-substituted amino group. Japanese Patent Provisional Publication No. 291569/1990 discloses a toner incorporating a coloring agent resulting from treatment of a xanthene dye with a compound having a phenolic OH group. Japanese Patent Provisional Publication No. 266462/1988 discloses toners containing a compound such as 2,6-di-tertiary-butyl-p-cresol,
2,6-di-tertiary-butyl-4-ethylphenol,
2,2'-methylene-bis-(4-methyl-6-tertiary-butylphenol) or
2,2'-methylene-bis-(4-ethyl-6-tertiary-butylphenol).

However, the developing agents incorporating such a toner do not have sufficient chargeability, though they are excellent in fixability, offset resistance and durability.

The object of the present invention, developed in view of the above problems involved in conventional methods, is to provide a charge control agent which is good in heat resistance, pulverizability and resin affinity and dispersibility, excellent in charge control property stability to changes in temperature and humidity, i.e., environmental resistance, and stability of charge control property over time, i.e., storage stability, versatile for use in color toners, including the three subtractive primaries yellow, magenta and cyan colors, and safe to the human body, and a toner for developing electrostatic images which is excellent in environmental resistance and storage stability with respect to chargeability and can be used as a toner with various chromatic or achromatic colors.

Although one of the present inventors has already developed the invention disclosed in Japanese Patent Provisional Publication No. 201378/1990, the present invention is directed to providing a charge control agent offering more rapidly rising charging and a toner of developing electrostatic images permitting a more rapid rise of charging.

SUMMARY OF THE INVENTION

The active ingredient of the charge control agent of the present invention is a calix(n)arene compound represented by the following formula [I].

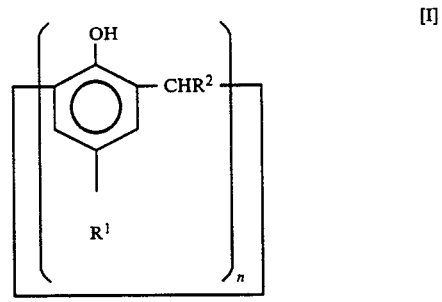

wherein
$R^1$ represents an alicyclic group; $R^2$ represents a hydrogen atom, an alkyl group having 1 to 4 carbon atoms or aryl group; and
n represents an integer of 1 to 8.

The toner for developing electrostatic images of the present invention incorporates at least one kind of the charge control agent as described in connection with formula [I], and a coloring agent and a resin. In other words, the toner for developing electrostatic images may contain one kind of the charge control agent described above and may contain two or more kinds of the charge control agent.

The charge control agent of the present invention is good in heat resistance, pulverizability and resin affinity and dispersibility, high in charge providing performance, narrow in dispersion (distribution) of the amount of charges provided, excellent in environmental resistance and storage stability, and even when used in various chromatic or achromatic toners, it causes almost no color tone damage in the toner image, and it is safe to the human body. Also, because the charge control agent of the present invention makes it possible to realize a rapid rise of charging, it is highly effective in the speed-up and improvement in the quality of initial image in electrophotography etc.

In addition, containing this charge control agent, the toner for developing electrostatic images of the present invention is high in chargeability, narrow in the dispersion (distribution) of the amount of charges, and excellent in environmental resistance and storage stability with respect to charging property, and it can be used for various chromatic or achromatic colors and is safe to the human body. Also, because of a rapid rise of charging, the toner for developing electrostatic images of the present invention is highly effective in the speed-up and improvement in the quality of initial image in electrophotography etc.

DETAILED DESCRIPTION OF THE INVENTION

Figure 1:
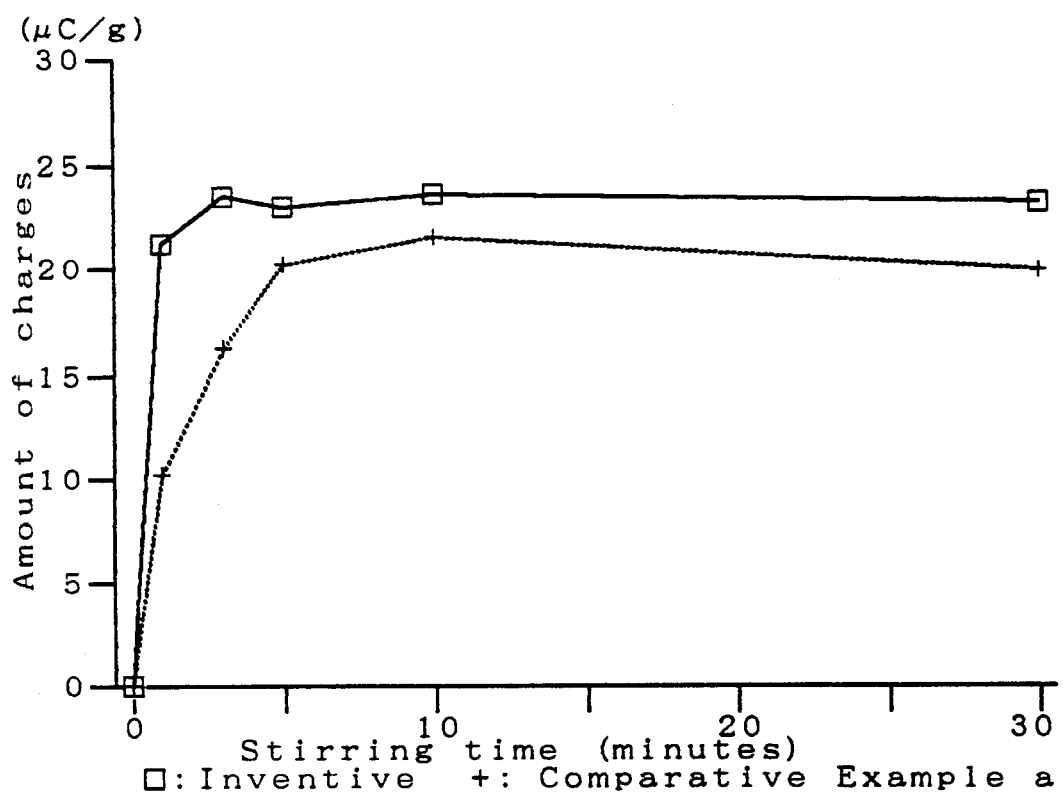
FIG. 1 is a graph showing the charge rise characteristics of a sample according to the present invention and a comparative sample.

Calixarene compounds have a cylindrical structure similar to that of cyclodextrin. For example, given calixarene compound usable as a charge control agent according to the invention can be obtained with high yield when it is prepared from the starting materials phenol and formaldehyde in the presence of high concentration of alkali.

Zinke et al. found that reaction of phenol and formaldehyde in the presence of sodium hydroxide yields a high melting substance. Then, Gutsche et al. presented a detailed report on the production, structure and physical properties of various calix(n)arene derivatives [J. Am. Chem. Soc., 103, 3782 (1981)].

$R^1$ is exemplified by alicyclic groups (alicyclic saturated hydrocarbon groups) such as cyclopropyl, cyclobutyl, cyclopentyl, cyclohexyl, cycloheptyl and cyclooctyl, e.g. a cycloalkyl group having 3 to 8 ring carbon atoms.

When formaldehyde is used as a starting material, $R^2$ is exemplified by a hydrogen atom. When alkylaldehyde is used, $R^2$ is an alkyl group such as methyl, ethyl, propyl or butyl. When benzaldehyde is used, $R^2$ is a phenyl group. $R^2$ may be an aryl group, e.g. having 6 to 10 ring carbon atoms, such as a phenyl or naphthyl group.

A calix(n)arene compound represented by Formula I can be synthesized in accordance with the methods described in the following references:
1) J. Am. Chem. Soc., 103 3782-3792 (1981).
2) Pure and Appl. Chem., Vol. 58, No. 11 1523-1528 (1980,).
3) Tetrahedron Letters, Vol. 26, No. 28 3343-3344 (1985).
4) Gendai Kagaku, 182, 14-23 (1986).

When a calix(n)arene compound is synthesized in accordance with an ordinary method of synthesis, a mixture of a cyclic n-mer and an acyclic product is produced. A calix(n)arene compound of Formula I can be obtained by isolating the desired cyclic product from this mixture by recrystallization etc., It is speculated that the above-mentioned acyclic product is, for example, an oligomer represented by the following formula [II]:

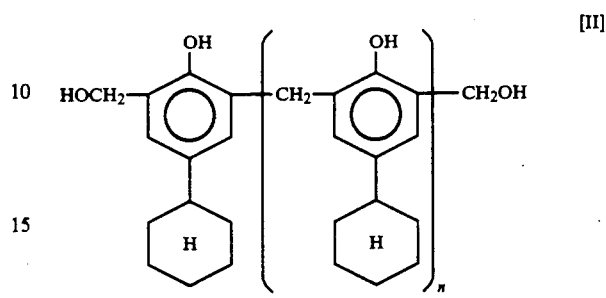

wherein n represents an integer of 2 to 8.

This acyclic product is different from, for example, the p-cyclohexylcalix(n)arene of the present invention in physical properties and structure, exhibiting almost no charge control performance.

Examples of alkalis which can be used to synthesize a calix(n)arene compound of Formula [I] include sodium hydroxide, potassium hydroxide and rubidium hydroxide. Synthesis reaction temperature is preferably 130° to 200° C. Examples of usable solvents include xylene, mesitylene and diphenyl ether.

SYNTHESIS EXAMPLE 1

Synthesis of p-cyclohexylcalix(8)arene [Example Compound (1)]

11.3 g of p-cyclohexylphenol and 4.4 g of p-formaldehyde were refluxed and dehydrated in 120 ml of xylene for 8 hours in the presence of 0.6 ml of 10N potassium hydroxide. After cooling, this mixture was filtered.

The residue was washed with toluene, ether, acetone and water in this order, and then dried.

The dry product was recrystallized using chloroform to yield 6.9 g of white needles (yield 57%).

SYNTHESIS EXAMPLE 2

Synthesis of p-cyclohexylcalix(6)arene [Example Compound (3)]

11.3 g of p-cyclohexylphenol and 4.4 g of p-formaldehyde were refluxed and dehydrated in 100 ml of xylene for 6 hours in the presence of 1 ml of 5N rubidium hydroxide. After cooling, this mixture was filtered.

The residue was separated using chloroform-hydrochloric acid and then recrystallized to yield 5.4 g of white powder (yield 44%).

SYNTHESIS EXAMPLE 3

Synthesis of p-cyclohexylcalix(8)arene derivative [Example Compound (8)]

11.3 g of p-cyclohexylphenol and 15.9 g of benzaldehyde were refluxed and dehydrated in 150 ml of mesitylene for 4 hours in the presence of 0.6 ml of 10N potassium hydroxide. After cooling, this mixture was filtered.

The residue was washed with toluene, ether, acetone and water in this turn, and then dried.

The dry product was recrystallized using chloroform to yield 11 g of white powder (yield 59%).

Examples of the calix(n)arene compound represented by Formula [I] are shown below, which are not to be construed as limitative. All of them can be preferably used as charge control agents.

Example Compound (1) [p-cyclohexylcalix(8)arene of Formula [I] wherein $R^1$ is a cyclohexyl group, $R^2$ is a hydrogen atom, and n is 8.]

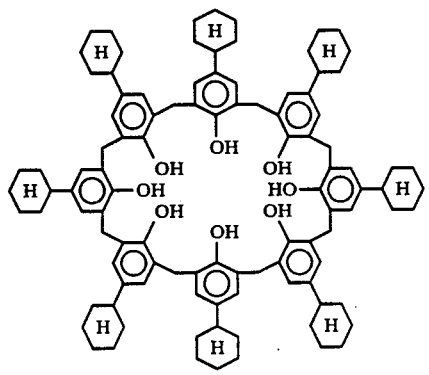

(2)

Example Compound (2) [p-cyclohexylcalix(7)arene of Formula [I] wherein $R^1$ is a cyclohexyl group, $R^2$ is a hydrogen atom, and n is 7.]

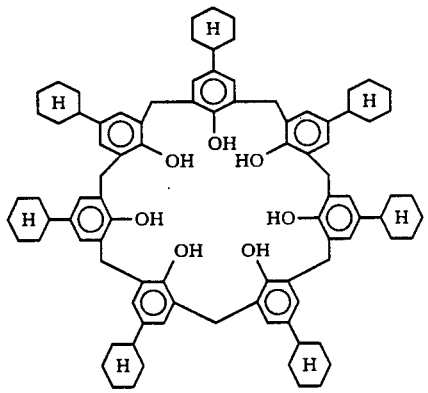

Example Compound (3) [p-cyclohexylcalix(6)arene of Formula [I] wherein $R^1$ is a cyclohexyl group, $R^2$ is a hydrogen atom, and n is 6.]

(3)

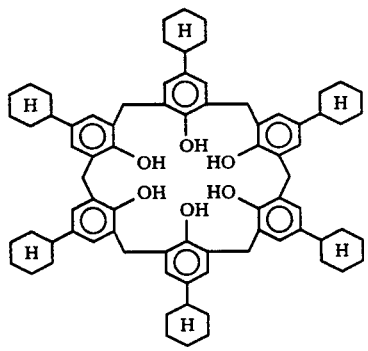

Example Compound (4) [p-cyclohexylcalix(5)arene of Formula [I] wherein $R^1$ is a cyclohexyl group, $R^2$ is a hydrogen atom, and n is 5.]

(4)

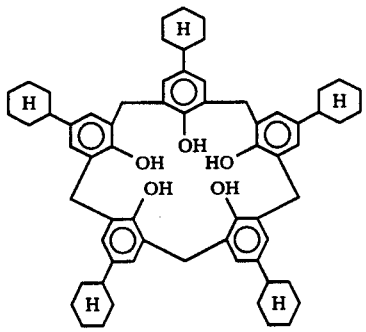

Example Compound (5) [p-cyclohexylcalix(4)arene of Formula [I] wherein $R^1$ is a cyclohexyl group, $R^2$ is a hydrogen atom, and n is 4.]

(5)

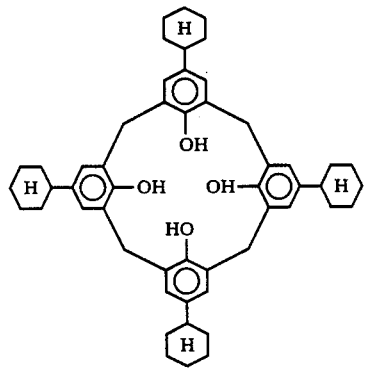

Example Compound (6) [p-cyclohexylcalix(8)arene derivative of Formula [I] wherein $R^1$ is a cyclohexyl group, $R^2$ is an ethyl group, and n is 8.]

(6)

Example Compound (7) [p-cyclopentylcalix(8)arene of Formula [I] wherein $R^1$ is a cyclopentyl group, $R^2$ is a hydrogen atom, and n is 8.]

(7)

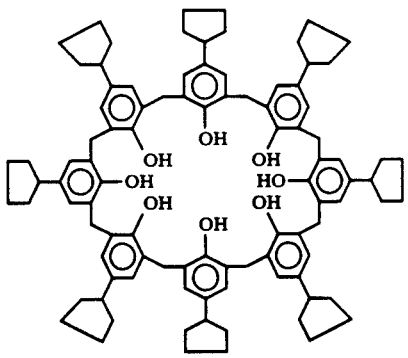

Example Compound (8) [p-cyclohexylcalix(8)arene derivative of Formula [I] wherein $R^1$ is a cyclohexyl group, $R^2$ is a phenyl group, and n is 8.]

(8)

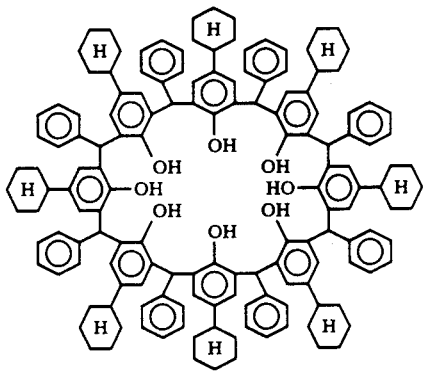

The toner for developing electrostatic images of the present invention desirably contains the charge control agent of the present invention in a ratio of 0.1 to 10 parts by weight, more preferably 0.5 to 5 parts by weight per 100 parts by weight of resin.

To improve toner quality, additives such as electroconductive grains, fluidity improving agents and image peeling preventing agents may be added internally or externally.

Examples of resins used in the toner of the present invention include the following known resins or binder resins for use in toners. Specifically, styrene resin, styrene-acrylic resin, styrene-butadiene resin, styrene-maleic acid resin, styrene-vinyl methyl ether resin, styrene-methacrylic acid ester copolymer, phenol resin, epoxy resin, polyester resin, polypropylene resin and paraffin wax may be used singly or in combination.

For preferable use of a resin or binder resin for toners in a toner used for full-color imaging by subtractive mixing or for OHP (overhead projectors) etc., the resin or binder resin is required to have special properties, for example, it should be transparent, substantially colorless (colored to such extent that toner images do not undergo tone deterioration), compatible with the charge control agent of the present invention, fluid under appropriate heat or pressure, and pulverizable.

Examples of such resins for preferable use include polystyrene resin, acrylic resin, styrene-acrylic resin, styrene-methacrylic acid ester copolymer and polyester resin.

The toner of the present invention may incorporate various known dyes and pigments as coloring agents. Examples of such dyes and pigments which can be used in color toners include organic pigments such as carbon black, quinophthalone, Hansa Yellow, Rhodamine 6G Lake, quinacridone, Rose Bengale, copper Phthalocyanine Blue and copper Phthalocyanine Green, various oil-soluble dyes and dispersion dyes such as azo dyes, quinophthalone dyes, anthraquinone dyes, xanthene dyes, triphenylmethane dyes and phthalocyanine dyes, and dyes and pigments processed with higher fatty acid, resin or another substance.

The toner for developing electrostatic images of the present invention may incorporate the above-mentioned coloring agents singly or in combination. Dyes and pigments having a good spectral property can be preferably used to prepare a toner of the three primaries for full-color imaging. Chromatic monocolor toners may incorporate an appropriate combination of a pigment and dye of the same color tone, such as a rhodamine pigment and dye, a quinophthalone pigment and dye, or a phthalocyanine pigment and dye.

The toner for developing electrostatic images of the present invention is, for example, produced as follows:

A toner having an average grain size of 5 to 20 μm can be obtained by thoroughly mixing a resin and coloring agent as described above, the charge control agent of the present invention, and, if necessary, a magnetic material, a fluidizing agent and other additives, using a ball mill or another mechanical mixer, subsequently kneading the mixture in a molten state using a hot kneader such as a heat roll, kneader or extruder, cooling and solidifying the mixture, and then pulverizing the mixture and classifying the particles.

Other usable methods include the method in which the starting materials are dispersed in a binder resin solution and then spray dried, and the polymerizing toner production method in which a given set of starting materials are mixed in a monomer for binder resin to yield an emulsified suspension which is then polymerized to yield the desired toner (e.g., the methods described in Japanese Patent Provisional Publication Nos. 260461/1989 and 32365/1990.

When using the toner of the present invention as a two-component developer, development can be achieved by the two-component magnetic brush developing process or another process using the toner in mixture with carrier powder.

Any known carrier can be used. Examples of the carrier include iron powder, nickel powder, ferrite powder and glass beads of about 50 to 200 μm in particle size, and such materials as coated with acrylic acid ester copolymer, styrene-acrylic acid ester copolymer, styrene-methacrylic acid ester copolymer, silicone resin, polyamide resin, ethylene fluoride resin or the like.

When using the toner of the present invention as a one-component developer, fine powder of a ferromagnetic material such as iron powder, nickel powder or ferrite powder may be added and dispersed in preparing the toner as described above. Examples of developing processes which can be used in this case include contact development and jumping development.

EXAMPLES

The present invention is hereinafter described in more detail by means of the following examples, but these are not to be construed as limitative on the present invention. In the description below, "part(s) by weight" are referred to as "part(s)" for short.

Example 1

Styrene-acrylic copolymer resin [HIMER SMB600 (trade name), produced by Sanyo Kasei Co., Ltd.] ... 100 parts Oil-soluble magenta dye [Oil Pink #312 (trade name), produced by Orient Chemical Industries Ltd.] ... 6 parts Low polymer polypropylene [Viscol 550-P (trade name), produced by Sanyo Kasei Co., Ltd.] ... 5 parts Example Compound (1) ... 1 part The above ingredients were uniformly premixed using a high-speed mixer, and then kneaded in a molten state using an extruder, cooled, and roughly milled in a vibration mill. The obtained coarse product was finely pulverized using an air jet mill equipped with a classifier to obtain a magenta toner of 10 to 20 μm in particle size.

5 parts of this toner was admixed with 95 parts of an iron powder carrier [TEFV 200/300 (trade name), produced by Nippon Teppun Co., Ltd.) to yield a developer.

This developer was found to be $-20.2$ μC/g in the amount of initial blowoff charge. The amounts of initial blowoff charges of this developer under low-temperature low-humidity condition (5° C., 30% relative humidity) and high-temperature high-humidity condition (35° C. 90% relative humidity) were $-20.4$ μC/g and $-19.8$ μC/g, respectively, indicating very high environmental stability and good storage stability.

When this developer was used for a commercial copying machine (selenium drum type) to form toner images, fog-free distinct magenta color images with good thin-line reproducibility, excellent spectral property and transparency suitable for superposing color mixing were obtained.

Example 2

Polyester [produced by The Nippon Synthetic Chemical Industry, Co., Ltd.] ... 100 parts Quinoline dye [C.I. Disperse Yellow 64] ... 3 parts Low polymer polypropylene [Viscol 550-P (trade name), produced by Sanyo Kasei Co., Ltd.] ... 5 parts Example Compound (1) ... 1 part The above ingredients were treated in the same manner as in Example 1 to yield a yellow toner, which was then used to prepare a developer.

This developer was found to be $-21.0$ μC/g in the amount of initial blowoff charge. The amounts of initial blowoff charges of this developer under low-temperature low-humidity condition (5° C., 30% relative humidity) and high-temperature high-humidity condition (35° C. 90% relative humidity) were $-20.5$ μC/g and $-20.2$ μC/g, respectively, indicating very high environmental stability and good storage stability.

When toner images were formed in the same manner as in Example 1, this developer gave fog-free distinct yellow images with good thin-line reproducibility, excellent spectral property and transparency suitable for superposing color mixing.

When images copied on an OHP sheet were projected on a screen using OHP, distinct yellow pictures were obtained.

Example 3

Polyester [produced by The Nippon Synthetic Chemical Industry, Co., Ltd.] ... 100 parts Blue dye [(VALIFAST BLUE #2606 (trade name), produced by Orient Chemical Industries Ltd.] ... 2 parts Low polymer polypropylene [Viscol 550-P (trade name), produced by Sanyo Kasei Co., Ltd.] ... 5 parts Example Compound (3) ... 1 part The above ingredients were treated in the same manner as in Example 1 to yield a blue toner, which was then used to prepare a developer.

This developer was found to be $-21.3$ μC/g in the amount of initial blowoff charge. The amounts of initial blowoff charges of this developer under low-temperature low-humidity condition (5° C., 30% relative humidity) and high-temperature high-humidity condition (35° C. 90% relative humidity) were $-21.0$ μC/g and $-20.5$ μC/g, respectively, indicating very high environmental stability and good storage stability.

When images were formed in the same manner as in Example 1, this developer gave fog-free distinct yellow images with good thin-line reproducibility, excellent spectral property and transparency suitable for superposing color mixing.

Example 4

Styrene-acrylic copolymer resin [HIMER SMB600 (trade name), produced by Sanyo Kasei Co., Ltd.] ... 100 parts Carbon black [MA-100 (trade name), produced by Mitsubishi Chemical Industries, Ltd.] ... 5 parts Low polymer polypropylene [Viscol 550-P (trade name), produced by Sanyo Kasei Co., Ltd.] ... 5 parts Example Compound (3) ... 2 parts The above ingredients were treated in the same manner as in Example 1 to yield a black toner, which was then used to prepare a developer.

This developer was found to be $-23.1$ μC/g in the amount of initial blowoff charge. The amounts of initial blowoff charges of this developer under low-temperature low-humidity condition (5° C., 30% relative humidity) and high-temperature high-humidity condition (35° C. 90% relative humidity) were $-22.4$ μC/g and $-22.3$ μC/g, respectively, indicating very high environmental stability and good storage stability.

When images were formed in the same manner as in Example 1, this developer gave fog-free black images with good thin-line reproducibility.

Example 5

Styrene-2-ethylhexyl methacrylate copolymer resin (80/20) ... 100 parts

Triiron tetroxide [EPT-500 (trade name), produced by Toda Kogyo Corporation] ... 40 parts Low polymer polypropylene [Viscol 550-P (trade name), produced by Sanyo Kasei Co., Ltd.] ... 10 parts Carbon black [MA-100 (trade name), produced by Mitsubishi Chemical Industries, Ltd.] ... 6 parts Example Compound (8) ... 2 parts The above ingredients were uniformly premixed using a ball mill to yield a premix, which was then kneaded in a molten state at 180° C. using a twin-screw extruder [PCM-30 (trade name), produced by Ikegai Seisakusho Co., Ltd.], cooled and thereafter roughly crushed, finely pulverized and classified to yield a one-component toner of 5 to 15 μm in particle size.

When this toner was used for a commercial copying machine (produced by Canon Inc.) to form toner images, fog-free good-quality images with good thin-line reproducibility having a solid portion reflection density of 1.36.

Experiment for Comparison 1

A black toner and a developer of the present invention were prepared in the same manner as in Example 4 except that Example Compound (3) used in Example 4 was replaced with Example Compound (1).

Also, a black toner and a developer of Comparative Example a were prepared in the same manner as in Example 4 except that Example Compound 3 used in Example 4 was replaced with p-(n-hexyl)calix(8)arene.

To compare the toner charging rise characteristics, the amount of blow-off charge was measured with various developer stirring times. The results are shown in Table 1 and FIG. 1.

TABLE 1

| | Stirring time | | | | |
|---|---|---|---|---|---|
| | 1 minute | 3 minutes | 5 minutes | 10 minutes | 30 minutes |
| Inventive ($\mu$C/g) | −21.2 | −23.5 | −23.0 | −23.6 | −23.1 |
| Comparative Example a ($\mu$C/g) | −10.2 | −16.3 | −20.2 | −21.5 | −19.8 |

Experiment for Comparison 2

To compare toner chargeability, a comparative toner b was prepared in the same manner as in Example 1 except that Example Compound (1) used in Example 1 was replaced with 2,2'-methylene-bis-(4-ethyl-6-tertiary-butylphenol), which is disclosed in Japanese Patent Provisional Publication No. 266462/1988.

5 parts of this toner was admixed with 95 parts of an iron powder carrier (TEFV 200/300) to yield a two-component developer.

This developer was found to be −2.7 $\mu$C/g in the amount of initial blowoff charges.

Comparative toner b was found to have a lower charging rise speed and a smaller amount of charges, about 1/10 to ⅛, in comparison with the toner of the present invention.

What is claimed is:

1. A toner for developing an electrostatic image, comprising a resin, a coloring agent and a charge control effective amount of a charge control agent comprising a calix(n)arene compound of the formula

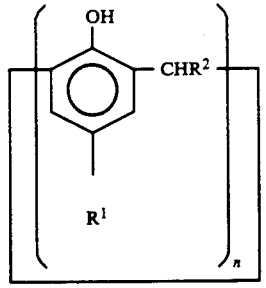

wherein $R^1$ is cycloalkyl having 3–8 carbon atoms, $R^2$ is hydrogen, alkyl having 1–4 carbon atoms or aryl having 6–10 ring carbon atoms, and n is 1–8.

2. Toner of claim 1 wherein $R^2$ is phenyl or naphthyl.

3. Toner of claim 1 wherein the charge control agent is present in an amount, by weight, of about 0.1 to 10 parts per 100 parts of the resin.

4. Toner of claim 1 wherein $R^1$ is cyclohexyl, $R^2$ is hydrogen and n is 8.

5. Toner of claim 1 wherein $R^1$ is cyclohexyl, $R^2$ is hydrogen and n is 7.

6. Toner of claim 1 wherein $R^1$ is cyclohexyl, $R^2$ is hydrogen and n is 6.

7. Toner of claim 1 wherein $R^1$ is cyclohexyl, $R^2$ is hydrogen and n is 5.

8. Toner of claim 1 wherein $R^1$ is cyclohexyl, $R^2$ is hydrogen and n is 4.

9. Toner of claim 1 wherein $R^1$ is cyclohexyl, $R^2$ is ethyl and n is 8.

10. Toner of claim 1 wherein $R^1$ is cyclopentyl, $R^2$ is hydrogen and n is 8.

11. Toner of claim 1 wherein $R^1$ is cyclohexyl, $R^2$ is phenyl and n is 8.

12. A toner for developing an electrostatic image, comprising a resin and a charge control effective amount of a charge control agent comprising a calix-(n)arene compound of the formula

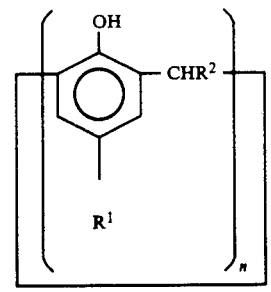

wherein $R^1$ is an alicyclic group, $R^2$ is a hydrogen atom, an alkyl group having 1–4 carbon atoms or an aryl group, and n is an integer of 2–8.

13. Toner of claim 12 wherein $R^1$ is selected from the group consisting of cyclopropyl, cyclobutyl, cyclopentyl, cyclohexyl, cychoheptyl and cyclooctyl.

14. Toner of claim 12 wherein $R^2$ is a phenyl or naphthyl group.

15. Toner of claim 12 wherein the charge control agent is contained in a ratio of 0.1 to 10 parts by weight per 100 parts by weight of the resin.

16. Toner of claim 12 wherein $R^2$ is a phenyl group.

17. Toner of claim 12 further comprising a colorant.

* * * * *